United States Patent
Fenton, Jr.

[11] Patent Number: 5,224,938
[45] Date of Patent: Jul. 6, 1993

[54] VALVED CATHETER

[75] Inventor: Paul V. Fenton, Jr., Marblehead, Mass.

[73] Assignee: Strato Medical Corporation, Beverly, Mass.

[21] Appl. No.: 853,569

[22] Filed: Mar. 18, 1992

[51] Int. Cl.$^5$ ............................................. A61M 25/00
[52] U.S. Cl. ........................................ 604/247; 604/9
[58] Field of Search .................. 604/236, 237, 9, 280, 604/247

[56] References Cited

U.S. PATENT DOCUMENTS

| | | | |
|---|---|---|---|
| 386,461 | 7/1888 | Goll | 137/527 |
| 2,867,213 | 1/1959 | Thomas, Jr. | 128/350 |
| 3,726,283 | 4/1973 | Dye et al. | 604/247 |
| 3,742,960 | 7/1973 | Dye et al. | 604/247 |
| 3,809,085 | 5/1974 | Bidwell | 604/247 |
| 4,180,068 | 12/1979 | Jacobsen et al. | 128/214 |
| 4,301,833 | 11/1981 | Donald, III | 137/527 |
| 4,327,722 | 5/1982 | Groshong et al. | 128/214 |
| 4,431,426 | 2/1984 | Groshong et al. | 604/280 |
| 4,493,696 | 1/1985 | Uldall | 604/43 |
| 4,549,879 | 10/1985 | Groshong et al. | 604/247 |
| 4,559,046 | 12/1985 | Groshong et al. | 604/282 |
| 4,589,869 | 5/1986 | Wernborg | 604/247 |
| 4,657,536 | 4/1987 | Dorman | 604/247 |
| 4,671,796 | 6/1987 | Groshong et al. | 604/247 |
| 4,701,166 | 10/1987 | Groshong et al. | 604/247 |
| 4,705,501 | 11/1987 | Wigness et al. | 604/43 |
| 4,753,640 | 6/1988 | Nichols et al. | 604/247 |
| 5,009,636 | 4/1991 | Wortley et al. | 604/280 |
| 5,030,210 | 7/1991 | Alchas | 604/247 |
| 5,147,332 | 9/1992 | Moorehead | 604/247 |
| 5,156,600 | 10/1992 | Young | 604/247 |

FOREIGN PATENT DOCUMENTS

| | | |
|---|---|---|
| 3512314 | 10/1986 | Fed. Rep. of Germany . |
| 2583386 | 12/1986 | France . |
| 1258396 | 12/1971 | United Kingdom . |
| 90/09204 | 8/1990 | World Int. Prop. O. . |

Primary Examiner—Paul J. Hirsch
Attorney, Agent, or Firm—Lahive & Cockfield

[57] ABSTRACT

A valved catheter is disclosed having an elongate, flexible tubular element defining a lumen extending along an axis substantially Parallel to the central axis of said tubular element, and a unidirectional valve assembly near its distal end which controls fluid flow in the tubular element. The valve is generally defined by a top flap portion and a base portion. The top flap portion includes a flap valve surface which is complementary to a base valve surface when there is substantially no pressure difference between the lumen and outside the catheter. When a pressure differential exists between the lumen and outside the catheter, the top valve surface and base valve surface separate to form an opening for fluid flow therethrough. The direction of fluid flow through the valve aperture is determined by the pressure differential. A multi-lumen catheter assembly is also disclosed.

21 Claims, 4 Drawing Sheets

VALVED CATHETER

BACKGROUND OF THE INVENTION

The present invention relates to a catheter intended for at least partial implantation within a living body for special or long term usage, and more particularly to a catheter having at least one unidirectional valve for controlling fluid flow into or out of the catheter.

Various medical procedures require vascular access over a period of time. Such procedures may include implantation of a permanent intravascular device for use with portable drug infusion devices, for hemodialysis, or for cases where continuous blood work or access to the bloodstream is required. These procedures are often performed by using either transcutaneous or totally implanted catheters.

It is desirable to limit the number of such devices intruding into the human body and it is also desirable to limit the possibility of infection, blood embolism and the like, by precluding diffusion of blood into the device when it is not in use.

To accomplish this, it is desirable to include a check valve integral with the catheter, so that when a pressure differential of a first sense is established across the catheter wall near its tip, a valve opens permitting fluid flow therethrough and when a pressure differential of the oppose sense is established, the valve closes and prevents fluid flow therethrough. Such check valves may be implemented to permit fluid flow either from the catheter or into the catheter.

These valved catheters, however, have multiple element valve assemblies resulting in a corresponding complexity.

A prior art catheter features a slit-type bidirectional check valve. The tip of the catheter is closed and the side wall of the catheter near the tip has a linear slit extending parallel to the central axis of the catheter, to form the slit valve. See U.S. Pat. No. 4,701,166. The valve allows both aspiration of blood and infusion of fluids depending upon the sense of the pressure differential across the catheter wall at the tip. The check valve precludes the diffusion of blood into the lumen when there is no pressure differential across the wall of the catheter. A catheter of this type is known as the Groshong catheter. While effective for some applications, this type of catheter typically has a very narrow range of pressure differentials at which no fluid flow occurs.

While various other valved catheters are also known, there is still a need for an improved, at least partially implantable, unidirectional valved catheter assembly which is easy to manufacture and easy to install in a patient, provides a distinct and reliable cut-off of reverse flow, and yet limits the possibility of infection, blood embolism, leakage and the like.

It is therefore an object of the present invention to provide an improved valved catheter which is easy to manufacture.

It is another object of the present invention to provide an improved catheter with at least one unidirectional valve.

Another object is to provide an improved bidirectionally valved catheter adapted for placement in the bloodstream.

SUMMARY OF THE INVENTION

The present invention provides an improved valved catheter which is easy to manufacture, installs easily and permits long term placement in a patient's bloodstream. The valves of the catheter provide distinct and reliable cut-off of reverse fluid flow therethrough. In one aspect of the invention, the valved catheter includes a lumen for fluid flow therethrough, and at least one valve assembly near its tip adapted for unidirectional (in either direction, as desired) flow of fluid between the lumen of the catheter and the outside of the catheter in response to a pressure differential established in a first sense across the catheter wall. The valve assembly of the invention prevents fluid flow between the outside of the catheter and the lumen of that catheter when a pressure differential is established in an opposite sense, or a zero differential is established.

Specifically, the valved catheter of the present invention includes an elongate, flexible tubular element which extends along a central axis, and defines a lumen extending along that central axis for fluid flow therethrough. The lumen of the tubular element may, for example, have a cross-section which is circular, oval D-shaped, or double-D (dual lumen).

The distal tip of the catheter is closed, and a valve assembly is positioned near the distal tip for fluidic communication between the lumen and the region exterior to the tubular element. The valve assembly includes at least one convex, beveled slit extending between two endpoints on the side wall of the tubular element. As used herein, the term convex slit may include a smooth curve or a piecewise linear curve. The convex, beveled slit defines a top flap portion at the sidewall having a flap valve surface, and a base portion of the sidewall having a base valve surface. The slit extends from the outer surface of the tubular element to the lumen defining the inner surface of the tubular element. The endpoints of the slit are positioned other than on an axis parallel to the central axis of the tubular element.

In a first, closed position, the flap valve surface and base valve surface are nominally opposed, adjacent and complementary. This first position occurs when there is substantially no pressure differential across the tubular element of the slit, or when the pressure differential across the slit has a first polarity (or sense) which biases the opposed flap and base valve surfaces together. When the pressure differential has a polarity opposite the first polarity, those surfaces are biased apart and the valve attains a second, open position, enabling fluid flow through the slit. Thus, the flap portion is displaceable in response to a pressure differential to selectively enable or disable fluid flow in a single direction between the lumen and the outer surface.

Thus, the valve is unidirectional. That is, depending on the construction of the specific catheter, flow may either be from inside the lumen through the valve out of the lumen, or from outside the lumen through the valve into the lumen. The direction of permitted flow depends on the angle of the slit bevel; reverse flow does not occur due to seating of the slit edges.

In a preferred embodiment of the invention, the tubular element is open at its proximal end and closed at its distal end. For an outflow (i.e., in-to-out flow) valve, the bevel is such that the flap portion lifts outward away from the tubular element in response to greater pressure within the lumen relative to pressure against the outer surface. The opposed valve surfaces that form the slit are forced away from each other to open the valve by relative elevation of pressure within the catheter. Thus, the valve facilitates fluid outflow when the static fluid pressure inside of the tubular element (i.e., within the lumen) is higher than the static fluid pressure outside of the tubular element by an amount sufficient to displace the opposed portions of the valve portions that form the slit.

In alternative embodiments, for example, the infusion valve may be formed such that the slit opens in response to a relatively low pressure within the lumen relative to the static fluid pressure exterior to the distal tip of the tube element. In that instance, the opposed valve surfaces are forced away from each other to open the valve by relative pressure outside the catheter.

Both types of unidirectional valves may be used in a single lumen-defining tubular element to establish a bidirectionally valved catheter.

In yet another embodiment, a multiple lumen catheter assembly may be established. Each lumen of such a catheter may include a valve assembly for selectively permitting fluid flow into one lumen, and another valve assembly for selectively permitting fluid flow out of another lumen. Alternatively, any or all of the valved lumens may include only a single such valve, adapted to permit flow in either direction, as desired. The lumina of such catheter assemblies may share common interior walls, and each lumen adapted for selective fluid flow in the same or different directions from the other.

BRIEF DESCRIPTION OF THE DRAWINGS invention will be more fully understood by reference to the following detailed description in conjunction with the attached drawings in which.

DETAILED DESCRIPTION OF THE PREFERRED EMBODIMENT

Figure 1:
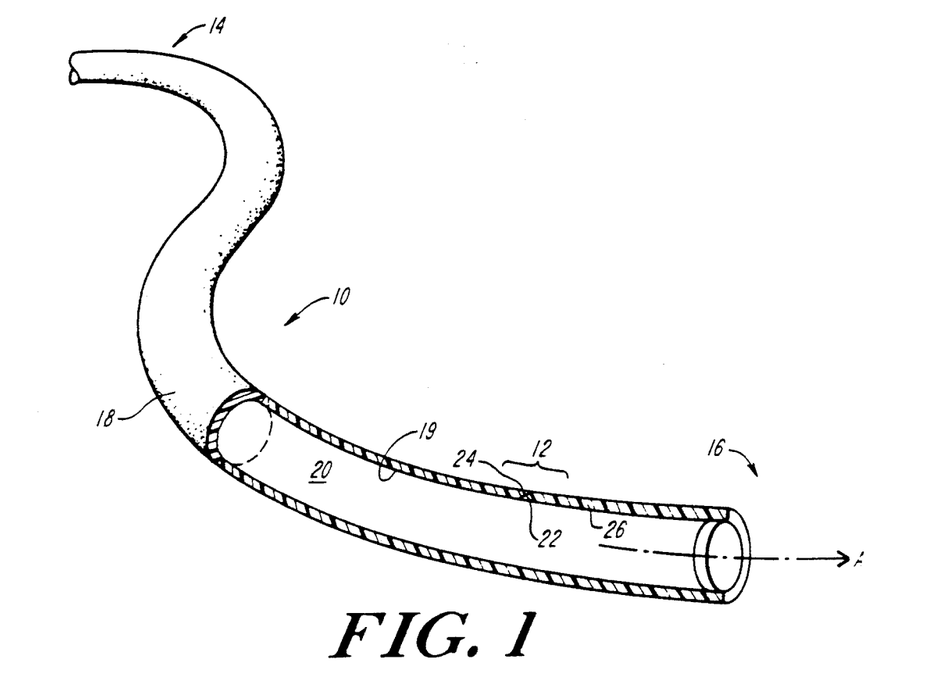
FIG. 1 shows, partially in cross-section and partially in perspective, a catheter assembly incorporating the present invention.
Figure 5A:
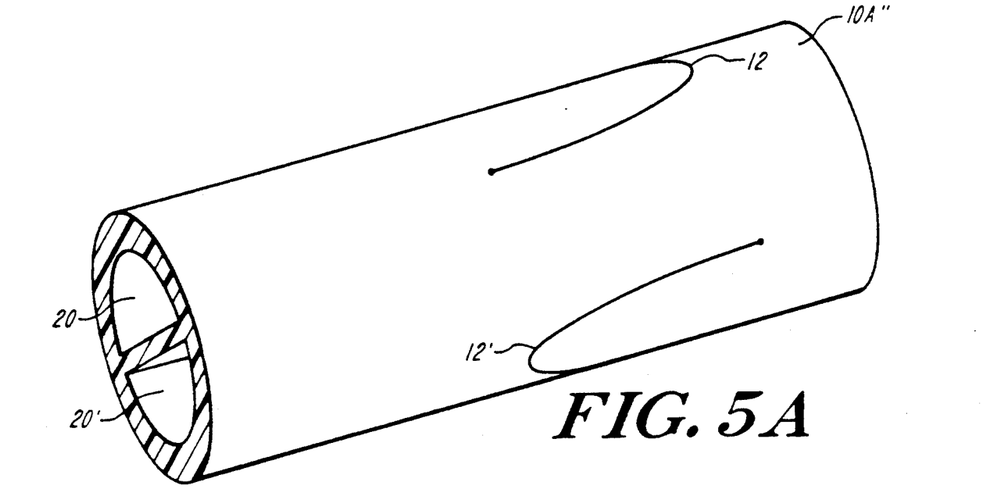
FIG. 5A is a perspective view of a dual lumen catheter, wherein each lumen has an associated valve assembly of the present invention.

A single lumen, unidirectional (outflow) valved vascular catheter embodying the invention is shown in FIG. 1 in which a flexible and resilient tubular element 10, such as a catheter, defines an elongate wall member 18, whose interior surface 19 defines a central lumen 20 extending along a central axis A. The catheter is preferably formed of biocompatible material such as silicone or polyurethane. In the embodiment of FIG. 1, the cross-section of lumen 20 is preferably circular or oval, but other shapes may also be used. For example, a "D" shaped cross-section is particularly useful for a dual lumen embodiment, as shown in FIG. 5.

The catheter has an open first or proximal end 14 and a closed second or distal end 16, and is adapted for inflow (infusion) of fluid from proximal end 14 to a point near distal end 16 and into a patient's bloodstream. Alternatively, the catheter may be adapted for outflow (aspiration) of fluid from the patient's bloodstream from a point near distal end 16 to proximal end 14. Central lumen 20 terminates at the catheter proximal end 14, which may be fitted with a conventional coupling device to facilitate coupling the catheter proximal end to a syringe or other extracorporeal equipment or to an implanted vascular access port, for example.

A unidirectional (outflow) valve assembly 12 is formed at a point along the catheter 10, preferably near to catheter distal end 16. Valve assembly 12 generally consists of a convex, beveled slit 22, forming a flap portion 24 and a base portion 26, both in the sidewall 18 of tubular element 10. As described more fully below, depending on the slit geometry for various embodiments, fluid infusion may be implemented under a "positive" pressure differential across the portion of element 10 bearing slit 22. Such pressure differential may be established by a device, such as a syringe or an infusion pump at the catheter proximal end 14. Fluid aspiration may be implemented under a "negative" pressure differential across the portion of element 10 bearing the slit 22 such as may be generated by hemodialysis pump. As used herein, the term "positive pressure differential across the slit" refers to those instances when the static pressure in the lumen 10 at the slit 22 is greater than the static pressure in the region adjacent to the slit 22 but outside element 10. Conversely, as used herein, the term "negative pressure differential across the slit" refers to those instances when the static pressure in lumen 20 is less than the static pressure in the region adjacent to the slit but outside element 10.

Figure 3A:
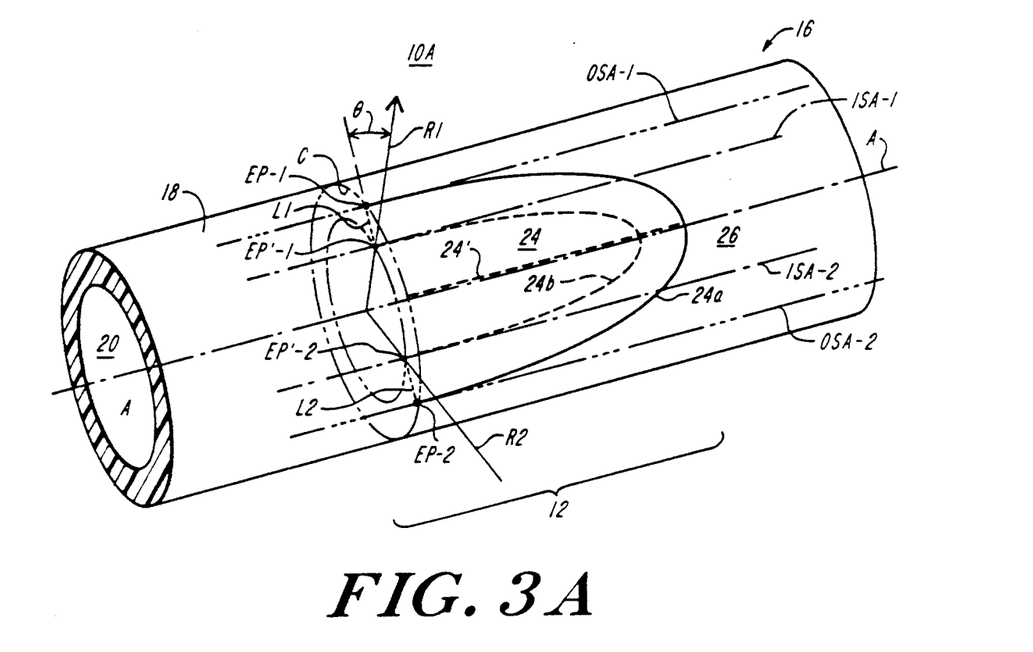
FIG. 3A is a perspective view of a catheter incorporating the valve assembly of the present invention having a beveled surface to permit selective fluid outflow.
Figure 3B:
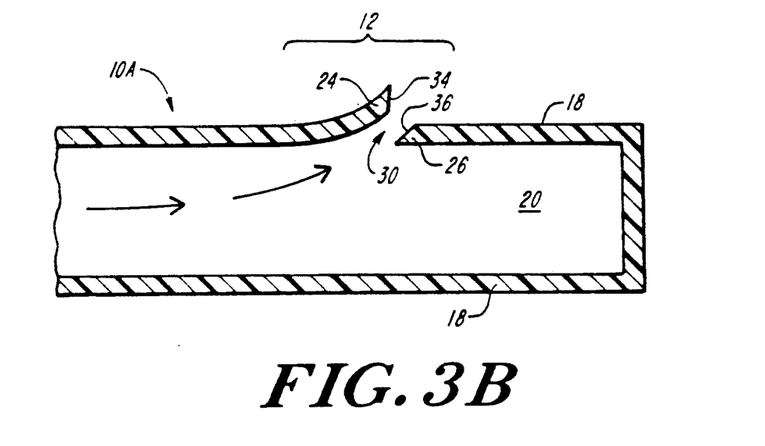
FIG. 3B shows in longitudinal cross-section the unidirectional valve of the embodiment of FIG. 3A having a beveled surface to permit selective fluid outflow.

In a neutral (or nominal) condition, where little or no pressure differential exists across the wall member 18, the surfaces that define the slit 22 are opposed, adjacent and complementary, so that the top flap portion 24 normally fits against the base portion 26. In this configuration, the valve assembly 12 permits fluid outflow (i.e., from lumen 20 to a region external to the lumen), for example, as shown in the embodiment of FIGS. 3A and 3B. In this embodiment, valve assembly 12 may be closed to fluid inflow (i.e., into lumen 20 from the surrounding tissue of the recipient patient).

The valve assembly 12 of FIGS. 3A and 3B includes a top flap portion 24, having a flap valve surface 34 which is complementary to a base valve surface 36 of the base portion 26. In the closed position, as illustrated in FIG. 3A, the flap valve surface 34 lies substantially flush against base valve surface 36 to prevent fluid flow out of, or blood flow into lumen 20. The material of the wall member 18 is substantially flexible and resilient to permit the top flap portion 24 to bend outwardly in response to a positive pressure differential across the slit, thus lifting flap valve surface 34 from resting against complementary base surface 36. As described below in conjunction with FIGS. 3A and 3B, when the top flap 24 is thus lifted, a valve opening 30 is formed through which fluid flows from the lumen 20 into the circulatory system of the recipient patient.

Figure 2:
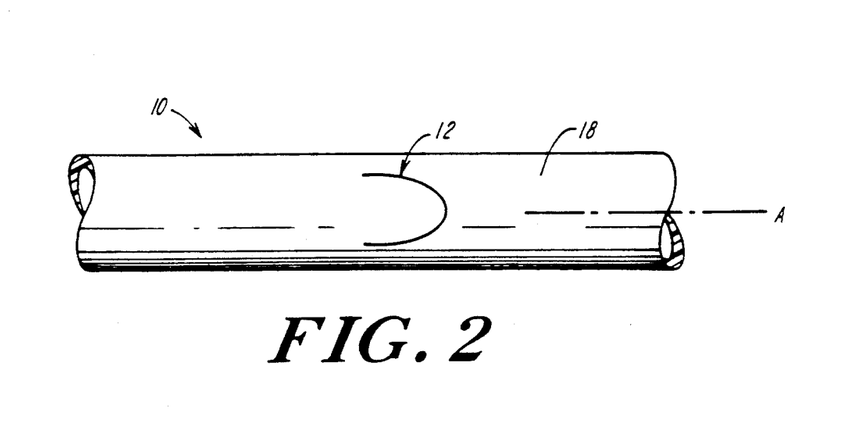
FIG. 2 shows a top plan view of a catheter assembly incorporating the valve assembly of the present invention.
Figure 4A:
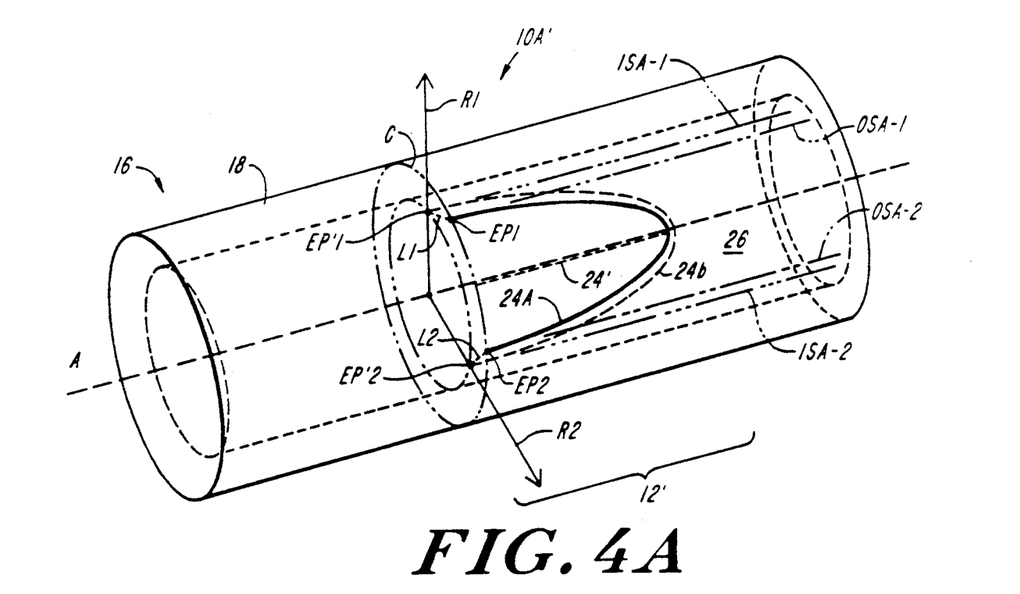
FIG. 4A is a perspective view of a catheter incorporating the valve assembly of the present invention having a beveled surface to permit selective fluid inflow.
Figure 4B:
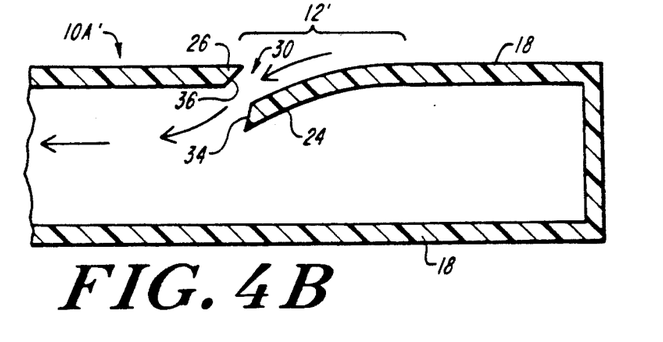
FIG. 4B shows in longitudinal cross-section the unidirectional valve of the embodiment of FIG. 4A having a beveled surface to permit selective fluid inflow.

In an alternative embodiment shown in FIGS. 4A and 4B, the bevel angle of the slit is reversed so that, the flap portion 24 may be moved inward into the lumen 20 to permit fluid flow into the lumen 20 from a source outside of the lumen, such as the circulatory system of the recipient patient. In a manner similar to that for the illustrated embodiment of FIG. 1 and 2, the flap valve surface 34 of the flap portion 24 lies substantially flush against the complementary base surface 36 of the base portion 26 when substantially no pressure differential or a positive pressure differential, exists across the valve assembly 12. As described below in conjunction with FIGS. 4A and 4B, upon application of a negative pressure (relative to the region at the slit outside the tubular element 10) a negative pressure differential is established across the flap portion 24. In response, the valve surface 34 moves away from base surface 36, inward into lumen 20. This, in turn, introduces valve opening 30 to permit fluid flow from outside the valve assembly 12 to inside the catheter lumen 20.

FIG. 3A shows a segment 10A of tubular element 10 including the distal end 16 and the valve assembly 12 near that end. The valve assembly 12 in the illustrated embodiment is adapted for selective unidirectional flow out of lumen 20. As shown, the segment 10A extends along central axis A. A circumferential axis C extends about the circumference of segment 10A near the distal end 16 and lies in a plane perpendicular to the central axis A. Two outer surface axes OSA-1 and OSA-2 extend along the outer surface of element 10 in a direction parallel to the central axis A, intersecting axis C at outer surface points EP-1 and EP-2, respectively.

The valve assembly 12 includes flap portion 24 and base portion 26 of sidewall 18 of tubular element 10, and a slit established by the adjacent edges of those portions. The edge of flap portion 24 is defined by a flap valve surface 34 extending from the outer surface to the inner surface of element 18 and from a first line L1 (connecting outer surface endpoint EP-1 and inner surface endpoint EP'-1 of segment 10A) to a second line L2 (connecting outer surface endpoint EP-2 and inner surface endpoint EP'-2 of segment 10A). The outer surface edge 24a of the flap valve surface 34 is a convex curve extending from endpoint EP-1 to endpoint EP-2, and lies substantially wholly between surface axes OSA-1 and OSA-2. Similarly, the inner surface edge 24b is a convex curve extending from endpoint EP'-1 to endpoint EP'-2, and lies substantially wholly between inner surface axes ISA-1 and ISA-2. This configuration establishes a convex slit. While in the preferred embodiment, the "convex" curves are smooth, they might alternatively be piecewise linear, or a continuous combination of curves and straight segments (such as U-shaped).

The base portion 36 is defined by a base valve surface that is normally opposite, adjacent and complementary to flap valve surface 34. The lines L1 and L2 are each separated by a respective one of rays R1 and R2 (which extend radially outward from axis A in the plane of circumferential axis C) by a monotonically increasing function of the distance (r) from axis A. As shown, that connection increases linearly with r, but other monotonically increasing functions may be used in other embodiments.

In the illustrated embodiment of FIGS. 3A and 3B, in which the valve assembly is adapted for selective unidirectional outflow from lumen 20, the length of the outer surface edge (24a) of flap portion 24 is greater than the length of the inner surface edge (24b) of flap portion 24, thereby establishing a beveled slit.

FIGS. 4A and 4B show an embodiment of a valve assembly 12' adapted for selective unidirectional inflow into lumen 20. All elements of the segment 10A' are the same as the corresponding elements of segment 10A, except that the length of the outer surface edge (24a) of flap portion 24 is less than the length of the inner surface edge (24b) of flap portion 24, thereby establishing a slit that is beveled in the opposite sense from that shown in FIGS. 3A and 3B.

In the embodiments of FIGS. 3A and 4A, the endpoints EP-1 and EP-2 are positioned in the C-axis plane perpendicular to central axis A, although in other embodiments different orientations of that plane may be used, other than an orientation parallel to axis A. Also, the edges of flap portion 24 of the embodiments of FIGS. 3A and 4A are transversely symmetrical about a surface axis 24' on the outer surface of segment 10A; in other embodiments, non-symmetrical edges may be used.

Figure 4C:
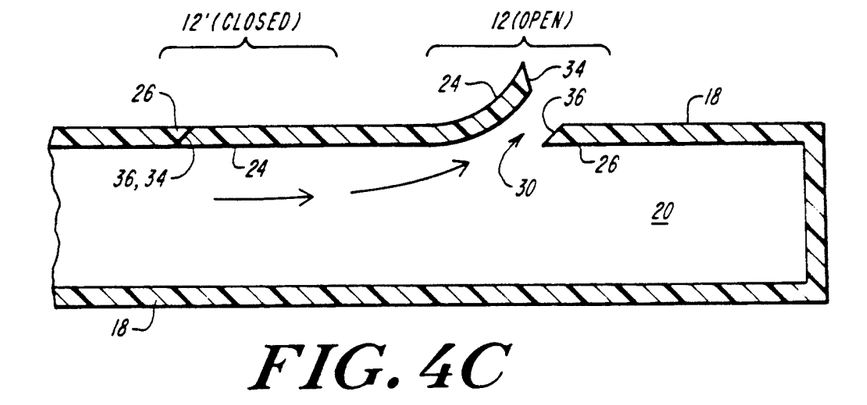
FIG. 4C shows in longitudinal cross-section of a catheter incorporating valve assembly of the present invention selectively permitting fluid inflow and outflow.

FIG. 4C shows the distal end of a catheter having an open outflow valve 12 (similar to that shown in FIGS. 3A and 3B) and a closed inflow valve 12' (similar to that shown in FIGS. 4A and 4B), thereby selectively permitting bidirectional flow in the catheter. In the preferred form, the outflow valve is between the inflow valve and the distal end, although that positioning could be reversed.

In all of these embodiments, with the bevel of the slit, as established by the flap valve surface 24 and base valve surface 36, a pressure differential of a first sense (or polarity) biases those surfaces against each other (thereby closing the slit and preventing fluid flow there through); a pressure differential of the opposite sense (or polarity) biases those surfaces away from each other (thereby opening the slit and permitting fluid flow there through), as shown in FIGS. 3B and 4B. Thus, the valve assembly 12 of FIGS. 3A and 3B provides a unidirectional outflow valve in segment 10A and the valve assembly 12 of FIGS. 4A and 4B provides a unidirectional inflow valve in segment 10A'.

Figure 5B:
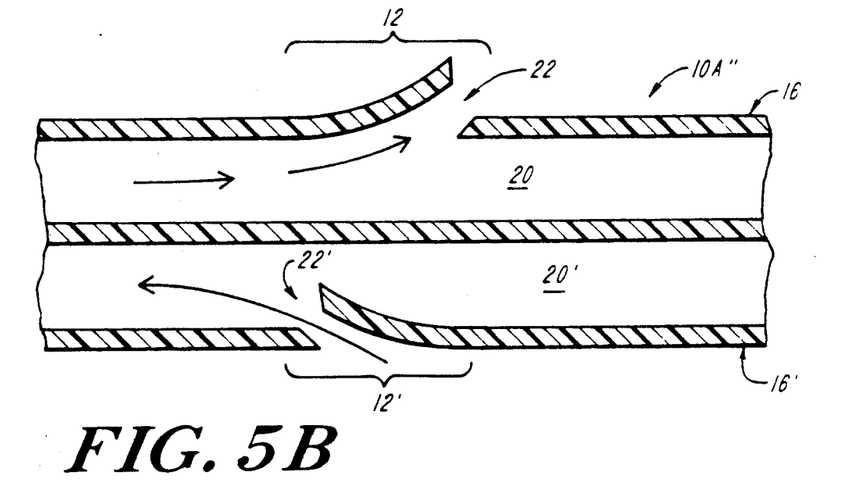
FIG. 5B shows in longitudinal cross-section the catheter of FIG. 5A.

FIGS. 5A and 5B show the distal end of a multiple lumen tubular element 10A" having one valve of each of the types of FIGS. 3A and 3B and FIGS. 4A and 4B, thereby Providing a bidirectionally valved catheter segment. The catheter of FIGS. 5A and 5B provides outflow from lumen 20 for a positive pressure differential across slit 22, inflow to lumen 20' for a negative pressure differential across slit 22', and no flow through the respective slits for substantially a zero pressure differential across the respective slits. In each case, there is a threshold pressure differential at which each flow valve opens, depending upon the stiffness and specific valve geometry. Thus lumen 20 of catheter 10" includes an aspiration valve assembly 12, and lumen 20' includes an infusion valve assembly 12', each of which may be operated independently.

With this configuration, a unidirectional valve assembly as described above may be advantageously employed in each lumen of a multi-lumen catheter, so as to afford independent unidirectional control to each of the multiple lumens. The additional lumens may include unidirectional valve assemblies of the type described above in conjunction with FIGS. 1–4B.

Figure 6:
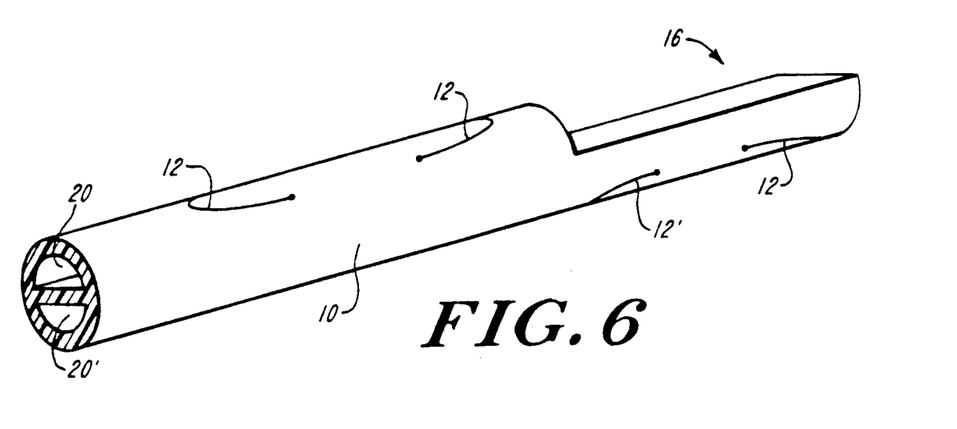
FIG. 6 is a perspective view of a dual lumen catheter, where each lumen has two associated valve assemblies of the present invention.

As a result of the foregoing, an easily formed and installed catheter can be formed with two independent, oppositely directed one way valve assemblies at the distal end of or more lumens at the catheter. Moreover, a multilumen catheter can be constructed with combinations of independent valved lumens, some being unidirectionally valved and some being bidirectionally valved. By way of example, FIG. 6 shows a dual lumen catheter (lumens 20 and 20') in which the distal end of lumen 20' extends beyond the distal end of lumen 20, and in which each lumen has an inflow valve and an outflow valve. The pressure in each lumen may be independently controlled at the proximal end so that each lumen may be operated in the same manner as the embodiment described in conjunction with FIG. 4C.

Patency of the catheter is maintained merely by saline flush. Since blood does not backflow into the infusion valve, the risk of forming emboli in the valve and subsequently inadvertently pumping them into the bloodstream during fluid infusion is substantially reduced. Thus the need for heparinization of this valve is alleviated.

An important aspect of the invention is the angle $\theta$ of the bevel of flap valve surface 34 and complementary base valve surface 36. Angle $\Gamma$ is measured with respect to ray R1. In a preferred embodiment, $35° < \theta < 55°$ (or $-35° < \theta < -55°$). Other angles may be used but angles $\theta = 0$; and $\theta = 90°$ are best avoided, although possible, since those valves could permit leakage at the end points of the slits.

The maintenance of a relatively uniform slit angle is important for preferred forms of the invention, particularly to accommodate intervals when there is substantially no pressure differential across the valve assembly. During these intervals, the flap valve surface 34 and base valve surface 36 are complementary such that they form a uniform seal to prevent fluid flow out of or into the lumen 20. If the angle of the slit varies, or tapers, as the pressure differential increases to open the valve, non-uniform opening may occur.

The amount of fluid pressure required to a valve assembly 30 for fluid transfer is primarily a function of the thickness and resiliency of the wall material, and the angle of the slit.

The present invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A catheter device, comprising:
   A. an elongate, flexible tubular element, said tubular element being open at its proximal end and being closed at its distal end, and having an outer surface and an inner surface, said tubular inner surface defining a first lumen extending along an axis substantially parallel to a central axis of said tubular element and adapted for selective flow of fluid therethrough;
   B. a first valve assembly near said distal end including means for selectively establishing fluid flow in a first direction between said lumen and the region adjacent to said outer surface near said distal end, said valve assembly including at least one convex, beveled slit defining a flap valve surface and a base valve surface, said flap valve surface and said base valve surface both extending from said outer surface to said inner surface and both extending from a first line connecting a first endpoint on said outer surface and a first endpoint on said inner surface and from a second line connecting a second endpoint on said outer surface and a second endpoint on said inner surface wherein said first and second endpoints on said outer surface are other than on an axis parallel to said central axis, and wherein said first and second endpoints of said inner surface are other than on an axis parallel to said central axis, said flap valve surface defining an edge of a flap portion of said tubular element, and said base valve surface defining an edge of a base portion of said tubular element, wherein the outer surface edge of said flap portion is substantially wholly between two axes on the outer surface of said tubular element, each of said outer surface axes being parallel to said central axis and passing through an associated one of said first and second endpoints on said outer surface, and the inner surface edge of said flap portion is substantially wholly between two axes on the inner surface of said tubular element, each of said inner surface axes being parallel to said central axis and passing through an associated one of said first and second endpoints on said inner surface, said flap and base valve surfaces being nominally opposed, adjacent and complementary when substantially no pressure differential exists across the portion of said tubular element bearing said slit and when a pressure differential exists across the portion of said tubular element bearing said slit, is of a first polarity such that said flap valve surface is biased toward said base valve surface, said flap valve surface and said base valve surface being biased apart otherwise;
   whereby said flap portion is displaceable in response to said pressure differential being of a polarity opposite said first polarity to enable fluid flow in said first direction between said lumen and the region adjacent to said outer surface near said distal end.

2. A catheter device according to claim 1 wherein for each point along said central axis underlying said flap portion, segments of rays extending perpendicularly from said central axis and passing through said inner surface edge are separated in a circumferential direction within said tubular element from said base valve surface by an increasing function of distance from said central axis.

3. A catheter device according to claim 2 has a greater length than said outer surface edge of said flap portion.

4. A catheter device according to claim 2 wherein said inner surface edge of said flap portion has a lesser length than said outer surface edge of said flap portion.

5. A catheter device according to claim 1 wherein said first and second endpoints on said outer surface are disposed along a circumferential axis of said tubular element.

6. A catheter device according to claim 5 wherein for each point along said central axis underlying said flap portion, segments of rays extending perpendicularly from said central axis and passing through said inner surface edge are separated in a circumferential direction within said tubular element from said base valve surface by an increasing function of distance from said central axis.

7. A catheter device according to claim 5 wherein said inner surface edge of said flap portion has a lesser length than said outer surface edge of said flap portion.

8. A catheter device according to claim 6 wherein said inner surface edge of said flap portion has a lesser length than said outer surface edge of said flap portion.

9. A catheter device according to claim 5:
where said outer surface edge of said flap portion is substantially symmetrical about a surface axis of said tubular element that is substantially Parallel to said central axis.

10. A catheter device according to claim 9 wherein for each point along said central axis underlying said flap portion, segments of rays extending perpendicularly from said central axis and passing through said inner surface edge are separated in a circumferential direction within said tubular element from said base valve surface by an increasing function of distance from said central axis.

11. A catheter device according to claim 10 wherein said inner surface edge of said flap portion has a greater length than said outer surface edge of said flap portion.

12. A catheter device according to claim 10 wherein said inner surface edge of said flap portion has a lesser length than said outer surface edge of said flap portion.

13. A catheter device according to claim 1 further comprising a second valve assembly near said distal end and including means for selectively establishing fluid flow in a second direction between said lumen and the region adjacent to said outer surface near said distal end, said second direction being opposite said first direction;
said second valve assembly comprising:
said second valve assembly including at least one convex, beveled slit defining a flap valve surface and a base valve surface, said flap valve surface and said base valve surface both extending from said outer surface to said inner surface, and both extending from a first line connecting a first endpoint on said outer surface and a first endpoint on said inner surface, and from a second line connecting a second endpoint on said outer surface and a second endpoint on said inner surface, wherein said first and second endpoints on said outer surface are other than on an axis parallel to said central axis, and wherein said first and second endpoints on said inner surface are other than on an axis parallel to said central axis, said flap valve surface defining an edge of a flap portion of said tubular element and said base valve surface defining an edge of a base portion of said tubular element, wherein the outer surface edge of said flap portion is wholly between two axes on the outer surface of said tubular element, each of said outer surface axes being parallel to said central axis and passing through an associated one of said first and second endpoints on said outer surface, and the inner surface edge of said flap portion is wholly between two axes on the inner surface of said tubular element, each of said inner surface axes being parallel to said central axis and passing through an associated one of said first and second endpoints on said inner surface, said flap and base valve surfaces being nominally opposed, adjacent and complementary when substantially no pressure differential exists across the portion of said tubular element bearing said slit and when a pressure differential exists across the portion of said tubular element bearing said slit is of a first polarity such that said flap valve surface is biased toward said base valve surface, said flap valve surface and said base valve surface being biased apart otherwise;
whereby said flap portion is displaceable in response to said pressure differential being at a polarity opposite said first polarity to enable fluid flow in said second direction between said lumen and the region adjacent to said outer surface near said distal end.

14. A catheter device according to claim 13 wherein said inner surface edge of said flap portion of said first valve assembly has a greater length than said outer surface edge of said flap portion of said first valve assembly, and
wherein said inner surface edge of said flap portion of said second valve assembly has a lesser length than the said outer surface edge of said flap portion of said second valve assembly.

15. A catheter device according to claim 14 wherein said second valve assembly is between said first valve assembly and said distal end.

16. A catheter device according to claim 1 wherein said inner surface edge of said flap portion has a greater length than said outer surface edge of said flap portion.

17. A catheter device according to claim 1 wherein said inner surface edge of said flap portion has a lesser length than said outer surface edge of said flap portion.

18. A catheter device according to claim 1 further comprising at least one additional lumen, each of said additional lumens including an additional first valve assembly substantially similar to said first valve assembly.

19. A catheter device according to claim 13 further comprising at least one additional lumen, each of said additional lumens including an additional first valve assembly substantially similar to said first valve assembly.

20. A catheter device according to claim 19 wherein at least one of said additional lumens includes an additional second valve assembly substantially similar to said second valve assembly.

21. A catheter device according to claim 20 wherein said additional second valve assemblies are between the respective ones of said additional first valve assemblies and said distal end.

* * * * *

UNITED STATES PATENT AND TRADEMARK OFFICE
CERTIFICATE OF CORRECTION

PATENT NO. : 5,224,938
DATED : July 6, 1993
INVENTOR(S) : Paul V. Fenton, Jr.

It is certified that error appears in the above-indentified patent and that said Letters Patent is hereby corrected as shown below:

Column 3, line 28, replace "...invention will be more fully understood" with --These and other advantages of the present invention will be more fully...--.

Column 7, line 25, replace Angle Γ is measured..." with --Angle $\theta$ is measured--.

Column 7, line 26, replace "...35° < O < 55°..." with --...35° < $\theta$ < 55°...--.

Column 7, line 27, replace "...-35° < O < -55°..." with --...-35° < $\theta$ < -55°...--.

In the Claims

In claim 3, column 8, lines 53-55, replace "A catheter device according to claim 2 has a greater length than said outer surface edge of said flap portion." with --A catheter device according to claim 2 wherein said inner surface edge of said flap portion has a greater length than said outer surface edge of said flap portion.--

Signed and Sealed this

Twenty-second Day of March, 1994

*Attest:*

BRUCE LEHMAN

*Attesting Officer*        *Commissioner of Patents and Trademarks*